United States Patent [19]

Muller et al.

[11] Patent Number: 5,239,257
[45] Date of Patent: Aug. 24, 1993

[54] MEASURING PROBE FOR AMPEROMETRIC DETERMINATION OF GASES AND/OR NONIONIC COMPOUNDS CONTAINED IN A MEASURED MEDIUM

[75] Inventors: Jorg Muller, Zurich; Urs Heber, Dietikon, both of Switzerland

[73] Assignee: Ingold Messtechnik AG, Urdorf, Switzerland

[21] Appl. No.: 781,244

[22] PCT Filed: Feb. 27, 1991

[86] PCT No.: PCT/CH91/00046
§ 371 Date: Dec. 23, 1991
§ 102(e) Date: Dec. 23, 1991

[87] PCT Pub. No.: WO91/16623
PCT Pub. Date: Oct. 31, 1991

[30] Foreign Application Priority Data

Apr. 24, 1990 [CH] Switzerland ............... 1383/90

[51] Int. Cl.$^5$ .................................. G01N 27/403
[52] U.S. Cl. .......................... 324/71.1; 204/415
[58] Field of Search ............ 324/425, 71.1; 204/415, 204/431, 153.16, 153.17

[56] References Cited

U.S. PATENT DOCUMENTS 3,577,332  5/1971  Porter et al. ............ 204/415 X
3,718,562  2/1973  Haddad .
4,252,627  2/1981  Ohashi et al. .

FOREIGN PATENT DOCUMENTS 0113966   7/1984  European Pat. Off. .
2178540A  2/1987  United Kingdom .
2218525A  11/1989 United Kingdom .

*Primary Examiner*—Jack B. Harvey
*Attorney, Agent, or Firm*—George Pappas

[57] ABSTRACT

A modular-construction measurement probe comprising a component designed as a diaphragm module and, connected to the diaphragm module, a rod electrode. The diaphragm is made up of at least three layers, the second layer having a much higher permeability than the first or third layer with respect to the gases and/or non-ionic compounds being determined. The first layer and the third layer are made of chemically resistant material. The three layers are preferably permanently bound to each other to give a uniform diaphragm structure, a support material in the form of stainless-steel gauze being mounted in the second layer. The probe is also fitted with a pressure-compensation system which makes it possible to compensate for pressure differences of the order of 20 bar which occur in operation between the measurement medium and the interior of the probe. The probe can therefore be steam-sterilized without problem. It is particularly suitable for use in the amperometric determination of oxygen.

13 Claims, 1 Drawing Sheet

MEASURING PROBE FOR AMPEROMETRIC DETERMINATION OF GASES AND/OR NONIONIC COMPOUNDS CONTAINED IN A MEASURED MEDIUM

TECHNICAL FIELD

The invention concerns a measuring probe for amperometric determination of gases and/or nonionic compounds contained in a measured medium, as well as the use of the measuring probe for the amperometric determination of oxygen in gas mixtures or fluids, and the use for amperometric determination of chlorine or hydrogen in gas mixtures or fluids.

BACKGROUND OF THE INVENTION

Membrane-covered measuring probes, specifically amperometric sensors are increasingly used for monitoring biological and biochemical processes as well as in the beverage and brewing industries, for determination of gases and/or nonionic compounds contained in a measured medium, for instance volatile ingredients of the measured medium or gases, specifically oxygen. To achieve an optimum function of such measuring probes, for instance a short response time, high sensitivity, low detection limit and good long-term stability, it is necessary to ensure that, e.g., pressure differences caused by temperature fluctuations between the measured medium and the interior of the measuring probe surrounding its sensitive parts will be extensively avoided or compensated for. Especially necessary for such measuring probes is to allow steam sterilization, so that the pressure differences occurring during steam sterilization will not affect the function of the measuring probe, i.e., measures are to be taken by which a deformation of the membrane due to high pressure differences between the measured medium and the probe interior will be prevented. In the case of measuring probes with a nonreinforced gas-permeable membrane, for instance as described in U.S. Pat. No. 2,913,386, a sufficient pressure stability can be achieved only with high equipment expense. To counteract the undesirable membrane deformation, various approaches were taken and the following measures applied:

a) pressure equalization using suitable devices;
b) maintenance of a pressure gradient from the measured medium toward the interior of the measuring probe;
c) reinforcement of the membrane.

The pressure equalization cited under a) is accomplished, for instance with the oxygen electrode described in U.S. Pat. No. 4,252,627 featuring an electrolyte-filled interior, in such a way that the probe housing is provided with an air gap via which the probe interior can communicate with the measured medium. A swift and exact pressure equalization can be achieved thereby; but it risks that volatile compounds can unimpededly penetrate the probe interior from the measured medium. This may cause a change of the electrolyte composition or, if no electrolyte is present, a change of the gas phase present in the probe interior, with the result of possible measuring errors in both cases.

The pressure equalization mentioned under a) may also be accomplished with the use of a flexible membrane or with the aid of a fluid drop, as described in U.S. Pat. No. 4,455,213, or by means of a piston moving in the probe housing. Besides, the pressure equalization can be accomplished by means of a valve which opens at a specific overpressure in the probe interior. This allows keeping the interior pressure within certain limits, but providing a valve causes a considerable equipment expense and, additionally, counter-acts a miniaturization of the probe, which for numerous applications is desirable.

The adjustment of a pressure gradient as mentioned under b) can be accomplished, e.g.. in that the probe interior is open toward the atmosphere causing the membrane to be forced on a backing, by the pressure of the measured medium. The membrane suffers then hardly a deformation, provided the roughness of the backing required for maintaining an electrolyte film is not selected excessively high and the pressure does not exceed a specific maximum value. In the case of probes where the interior is gas-filled, a satisfactory function is given only if the measurements will not be influenced by the penetration of atmospheric matter.

From the above comments it is evident that a sufficient pressure stability, and thus the prevention of an undesirable membrane deformation, can be accomplished with the measures cited under a) and b) only with considerable equipment expense. This applies to all measuring probes equipped with a single, nonreinforced gas-permeable membrane.

Less expense is required by the reinforcement of the membrane mentioned under c). The reinforcement may be accomplished, e.g., by embedding a backing material, for instance a netting or perforated panel from rugged material, for instance stainless steel, such as known from U.S. Pat. No. 3,718,562. This U.S. patent document concerns an electrode arrangement with a membrane made of selectively permeable material, for instance silicone caoutchouc, in which a porous interlacing is embedded as reinforcement. The reinforcement material is preferably a netting from an organic polymeric material or a steel net. Membranes of that type, especially when made of silicone caoutchouc are chemically not resistant, especially not to aggressive cleaning agents, and contaminate easily, for instance by bacterial growth when used in biological or biochemical processes, thereby impeding access of the gases or volatile compounds to be determined, to the sensitive parts of the measuring probe accommodated in its interior. When using, instead of a silicone caoutchouc membrane characterized by a high permeability, a membrane of fluorized hydrocarbon, for instance polytetrafluoro ethylene (PTFE) Teflon, it will be characterized by a very good chemical resistance, but have the disadvantage that its permeability to the gases to be determined will be by about two powers of ten lower than that of silicone caoutchouc.

Known from U.S. Pat. No. 3,718,562 is a polarographic measuring probe with a membrane consisting of two layers, where the first layer arranged on the medium side is formed by a material featuring a permeability that nearly equals that of silicone caoutchouc, while the second layer facing toward the probe interior is formed by a hydrophobic material whose permeability to gases and water vapor is considerably lower than that of the first layer. These layers are not interconnected; but they are fixed in the probe housing in such a way that a penetration of electrolyte solution and/or gases to be determined, into the space between the layers, will be prevented. This membrane structure achieves that the gas to be determined, which is used up on the cathode, will be much quicker replenished than is the case with a membrane formed of one layer, a so-called single membrane. Avoided this way, with the membrane formed of two layers, over long periods of time is an impoverishment of the gas to be determined, which yields exact measuring results and a short response time of the measuring probe equipped with this membrane. Unfavorable, however, is that the first layer arranged on the medium side, due to its material properties, is chemically little resistant and, when used in biological and biochemical processes, may easily be contaminated by bacterial growth.

To avoid the aforementioned disadvantages, the Swiss patent document . . . (application No. No. 02 503/88-9) proposed to make a membrane of two layers where the layer on the medium side is formed of a chemically resistant material and is insensitive to bacterial growth, and to integrate a backing material in the other layer formed of a material which in comparison to the material of the first layer possesses an increased permeability. The measuring probe equipped with this membrane favorably is distinguished from the aforementioned one by its chemical resistance, its insensitivity to contamination by bacterial growth, and by the stability of the membrane, but it is insufficiently insensitive to larger pressure differences between the measured medium and the probe interior, in case of applications requiring a steam sterilization of the measuring probe.

Therefore, the problem underlying the invention is to provide a measuring probe for determination of gases and/or nonionic compounds contained in a fluid or gaseous measured medium which is insensitive to pressure differences between the measured medium and the probe interior such as caused by temperature fluctuations, specifically in the course of steam sterilization, also in the range of $>10$ bars, and is additionally chemically resistant and dirt repellent.

This problem is inventionally solved by a measuring probe for amperometric determination of gases and/or non-ionic compounds contained in a measured medium, with an internal body accommodated within a probe interior defined by the probe housing, in which internal body an element sensitive to the gases and/or non-ionic compounds to be determined is integrated, and with a membrane terminating the probe interior housing, with the part of the probe housing supporting the membrane forming a membrane module which can be connected with an electrode shaft supporting the internal body, characterized in that the membrane consists of at least three layers where a first layer of chemically resistant material, facing in built-in condition toward the probe interior, is connected with a second layer on the surface of the first layer facing toward the probe interior, which second layer has in comparison with the first layer a greatly increased permeability to the gases and/or non-ionic compounds to be determined, while on its surface opposite the first layer there is a third layer arranged which completely covers the second layer and is formed by a material at least nearly equivalent to that of the first layer with regard to chemical resistance and permeability to the gases and/or non-ionic compounds to be determined, and in that in the membrane module there is a pressure equalization system integrated which at a pressure gradient occurring in operating condition between the measured medium and the probe interior is deformable in the direction of the pressure gradient.

Achieved by combining a membrane formed of at least three layers, where the middle layer, formed of a material which as compared to the material of the two outer layers displays a greatly elevated permeability to the gases and/or nonionic compounds to be determined—for simplicity hereafter called measured goods——and the two outer layers are chemically resistant and dirt-repellent, with a pressure equalization system integrated in the probe housing, is that a deformation of the membrane—also at pressure differences between the measured medium and the probe interior of approximately 20 bars—will be avoided practically completely, that a replenishment of measured goods used up at the cathode will be safeguarded without specific measures or equipment expense, thus avoiding an impoverishment of measured goods in the probe interior, and that damage to the membrane by the attack of aggressive chemicals as well as its contamination by bacterial growth will be prevented.

Another embodiment avoids a mutual separation of the layers while assuring an especially good stability of the membrane.

The selection of the material for the first and third layers and their combination with the second layer assures, for one, a high chemical resistance of the membrane surface which in operating condition makes contact with the measured medium and, for another, a sufficient replenishment of measured goods, due to the permeability differences between the materials chosen for the first and second layers, thereby avoiding an impoverishment of the measured goods in the probe interior in the case of prolonged measuring duration, and thus precluding an adulteration of measuring results.

Achieved by integration of a backing material in the middle, second layer, is an especially good form stability of the membrane, with a net from stainless steel being especially preferred.

The rigid fixing of the membrane and its sealing in the probe housing, causes the exchange of the gases and/or nonionic compounds to be determined to take place at the operating condition of the measuring probe exclusively via the membrane, while all other areas of the measuring probe are hermetically sealed from the measured medium and the surroundings, thus effectively precluding a penetration of contaminants, for instance of volatile substances contained in the measured medium or of atmospheric matter from the surroundings. This effect is greatly amplified yet by the embodiment, which additionally enables a simple measuring probe assembly.

The pressure equalization system enables a swift elimination of a pressure gradient between the measured medium and the probe interior in both directions.

Other embodiments, for one, assure a high insensitivity to the attack of aggressive chemicals, such as partly used in cleaning, and to the effect of elevated temperatures such as occurring during steam sterilization.

Besides, unevennesses or cracks in the surface of the probe housing, that might cause a contamination of the probe housing and bacterial growth, are avoided.

The measuring probe of the initially cited type can be used to particular advantage for the amperometric determination of oxygen in gas mixtures or fluids. But it can be used also for the determination of chlorine or hydrogen in gas mixtures and fluids.

DESCRIPTION OF THE DRAWINGS

Embodiments will be described hereafter with the aid of the drawings.

DESCRIPTION OF SPECIFIC EMBODIMENTS

Figure 1:
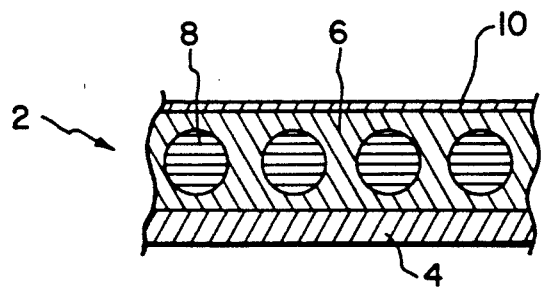
FIG. 1 shows a membrane in cross section.

FIG. 1 illustrates a membrane 2 comprised of three layers, which hereafter will be called triple membrane and which features a first layer 4, a second layer 6 in which a backing material 8, for instance a netting of stainless steel, is integrated, and a third layer 10. Facing in built-in condition toward the probe interior, the first layer suitably consists of a foil from a fluorized polymer, preferably of polytetrafluoro ethylene (PTFE), and has a thickness of maximally 0.1 mm. Arranged on the surface of the first layer 4 facing toward the probe interior is the second layer 6, which preferably is formed of silicone caoutchouc. The second layer 6 has a permeability to the gases to be determined, preferably oxygen, and/or the nonionic compounds which is approximately two powers of ten greater than that of the first layer 4. The netting of stainless steel integrated in the second layer 6 as backing material 8, which also may be replaced though by a netting or interlacing of a mechanically stable plastic material, has normally a thickness of 20 to 100 $\mu$m. The thickness of the net depends on the thickness of the second layer 6, which ranges from 30 to 150 $\|$ m. Arranged on the surface of the second layer 6, away from the first layer 4, is the third layer 10, which is formed of a foil from the same fluorized polymer as the first layer 4 or of a material which in terms of its permeability is similar, and it has a layer thickness that is smaller than that of the first layer 4 and normally amounts to 30 $\mu$m. The third layer 10 covers the adjacent second layer 6 completely, protecting in operating condition effectively from the attack of aggressive chemicals contained in the measured medium or used in cleaning and, due to the hydrophobic properties of the materials, it is dirt-repellent and protects against bacterial growth. The three layers are bonded to one another creating a unitary membrane 2. This can be accomplished in that the surfaces of the first layer 4 and of the third layer 10 facing toward the second layer 6 are during the fabrication of the membrane, prior to joining, hydrophilized or coated with a bonding agent. Hydrophilation can be accomplished, e.g; by etching.

Figure 2:
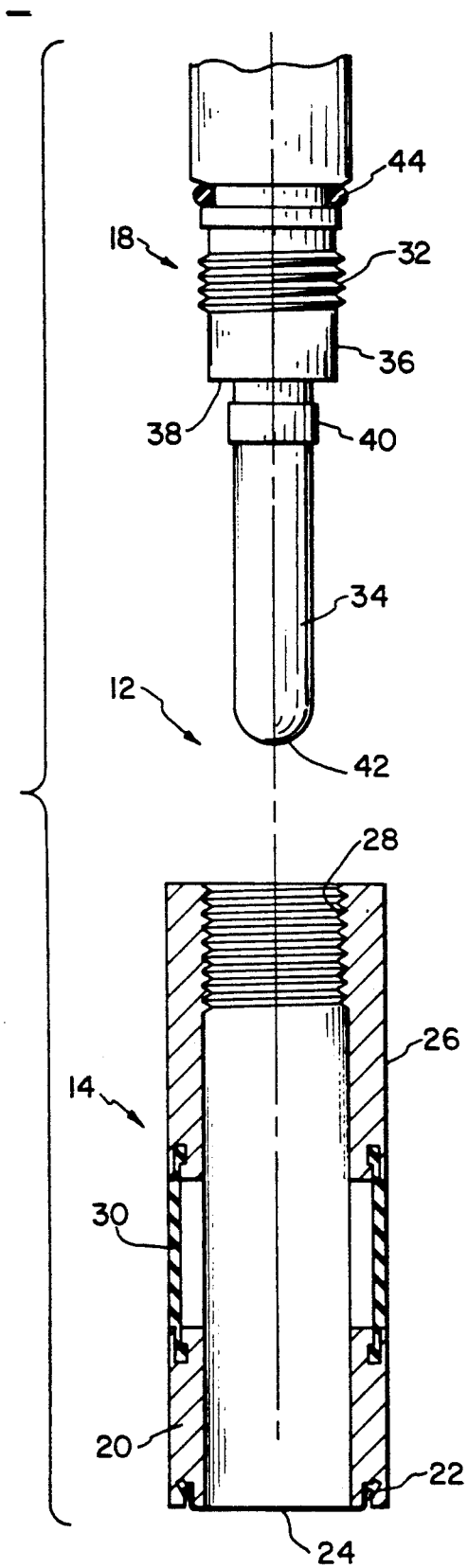
FIG. 2, a measuring probe in opened condition, partly in cross section.

FIG. 2 shows a measuring probe 12 usable for determination of gases and nonionic compounds contained in a measured medium; it features a membrane module 14 comprised of a tubular housing 16, for instance of stainless steel, and an electrode shaft 18. The membrane module 14 features in a first end section 20 a holder 22 for a membrane 24. The membrane 24 corresponds in its structure to that illustrated in FIG. 1 fashioned as a triple membrane 2 In a second end section 26 opposite to the end section 20 supporting the membrane 24, the membrane module 14 is provided with an internal threading 28. Additionally, between the first end section 20 and the second end section 26, there is a pressure equalization system 30 arranged which is formed by a hose of highly elastic, chemically and thermally resistant material, for instance a vulcanizable fluoroelastomer, and fitted in the wall of the housing 16. Connectable with the membrane module, the electrode shaft 18, consisting preferably of stainless steel, features an external threading 32 corresponding to the internal threading 28 of the membrane module 14 and allowing a simple screw-on of the membrane module 14 on the electrode shaft 18. Fastened in the electrode shaft 18 is an internal body 34, preferably of glass. Additionally, the electrode shaft 18 features a tubular extension 36 which partially surrounds the internal body 34 enveloping with it a cavity 38. In its section adjacent to the tubular extension, the internal body 34 features a first electrode 40, formed for instance by a silver ring and serving as anode. Moreover, the internal body 34 features a second electrode 42 forming the cathode; it is fastened in its end section away from the tubular extension 36 and formed preferably by a platinum wire molded into the internal body 34. Furthermore, the electrode shaft 18 possesses in its section adjacent to the external threading 32 and opposite to the tubular extension an O-ring seal 44 serving to outwardly seal the probe interior hermetically when screwed on the membrane module 14.

Figure 3:
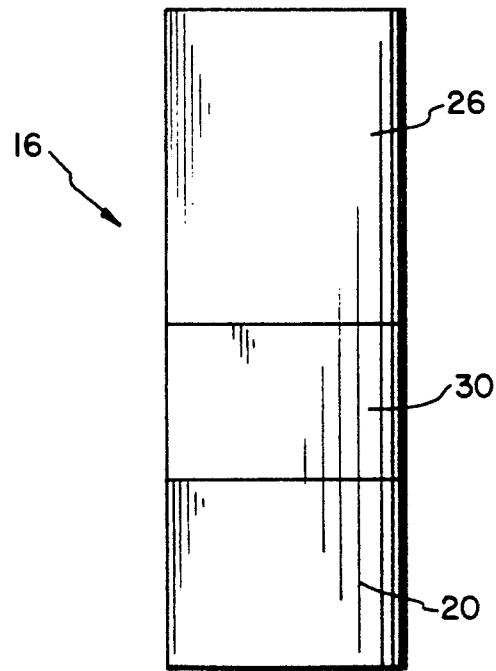
FIG. 3, a front elevation of the outside of the sectioned part of FIG. 2.

FIG. 3 is an outside view of the membrane module relative to FIG. 2, with the pressure equalization system 30 arranged between the end sections 20 and 26 of the housing 16. It evidences that the pressure equalization system is so fitted in the housing wall that the outer surface is smooth with no unevennesses or cracks in which dirt or bacteria might accumulate.

EXAMPLE

Membrane for a Measuring Probe for Oxygen Determination a) Membrane Structure

The triple membrane has the structure illustrated in FIG. 1 and is comprised of the following components:

A first PTFE layer with 25 $\mu$m thickness, a second silicone caoutchouc layer with 120 $\mu$m thickness in which a steel netting of 90 $\mu$m thickness is embedded, and a third PTFE layer with 6 $\mu$m thickness.

b) Membrane Function

The silicone caoutchouc layer is highly permeable and flexible displaying an outstanding adhesion to both of the adjacent layers of etched PTFE and the embedded steel netting. This assures a reliable bond between all three layers. Arranged on the medium side in operating state of the measuring probe, the PTFE layer provides outstanding protection for the silicone caoutchouc layer from the attack of hot lye, such as used for instance in breweries for cleaning, and from bacterial growth in the case of aerobic bioprocesses.

c) Membrane Fabrication

To begin with, the two layers made of PTFE are one-sidedly etched for superficial hydrophilation and improvement of their adhesion to the silicone caoutchouc layer to be placed in between. The steel netting is placed on the etched surface of the one PTFE layer. Next, a silicone caoutchouc paste is applied in such a way that the steel netting will be completely covered. Placed on the silicone caoutchouc layer is then the second PTFE layer, in such a way that its etched surface is opposite to the layer of silicone caoutchouc. The structure formed by the three layers is passed through a calender causing the displacement of excess silicone caoutchouc and impressing upon the structure a definitive thickness. Next, the resulting membrane structure is placed in a water bath, causing the polycondensation of the silicone caoutchouc. Once the polycondensation has completely run its course, the three layers will be inseparably bonded to one another forming a unitary membrane. The latter is then rigidly fixed in the housing of a measuring probe, in such a way that the probe interior surrounding the sensitive element integrated in the internal body, which in the case of the amperometric determination of oxygen is a precious metal cathode, will in the operating state of the measuring probe be hermetically sealed in relation to the measured medium.

d) Mode of Operation of the Measuring Probe

The response times of a measuring probe outfitted with a triple membrane described above were compared with those of a measuring probe equipped with a membrane according to U.S. Pat. No. 3,718,562. The latter membrane does not feature a layer from chemically resistant and dirt-repellent material arranged on the medium side. It is formed of a silicone caoutchouc layer with 120 μm thickness in which a steel netting 90 μm thick is embedded, and of a nonadhering PTFE layer bordering on the probe interior and having a thickness of 25 μm. For further comparison, a measuring probe with a so-called single membrane was used where the membrane consisted of a single PTFE layer with 60 μm thickness and of a steel net embedded in it that had a thickness of 30 μm. The following response times (90%) were recorded at 25° C:

| | |
|---|---|
| a) Triple membrane according to the above example | 50 seconds |
| b) Membrane according to U.S. Pat. No. 3 718 562 | 30 seconds |
| c) Single membrane | 4.6 minutes |

The comparison of response times shows that those with the triple membrane and according to the U.S. Pat. No. 3,718,562 are about equally good, whereas the response time of the measuring probe with a single membrane ranges considerably higher, and at that, nearly six times.

But when comparing the resistance to harmful chemical effects and to bacterial growth, it shows—as evidenced by comparative tests conducted in breweries and anaerobic bioprocesses—that the triple membrane mentioned under a) is significantly superior in terms of resistance to chemical effects, specifically the effect of hot lye, and in terms of bacterial growth of the membrane according to U.S Pat. No. 3,718,562 as mentioned under b). The medium side surface of the triple membrane displayed no damage whatsoever by chemical agents, specifically lyes, and was completely free of bacterial growth. The single membrane mentioned under c) displayed a similarly good resistance to chemical agents and bacterial growth; but due to its extraordinarily long response time it is unsuited for industrial use.

We claim:

1. A measuring probe for amperometric determination of gases and/or non-ionic compounds contained in a measured medium, with an internal body accommodated within a probe interior defined by the probe housing, in which internal body element sensitive to the gases and/or non-ionic compounds to be determined is integrated, and with a membrane terminating the probe interior and reinforced by a backing material while fixed in the probe housing, with the part of the probe housing supporting the membrane forming a membrane module which can be connected with an electrode shaft supporting the internal body, the membrane comprising three layers where a first layer of chemically resistant material, facing in built-in condition toward the probe interior, is connected with a second layer on the surface of the first layer facing toward the probe interior, which second layer has in comparison with the first layer a greatly increased permeability to the gases and/or non-ionic compounds to be determined, while on its surface opposite the fist layer there is a third layer which complete covers the second layer and is formed by a material at least nearly equivalent to that of the first layer with regard to chemical resistance and permeability to the gases and/or non-ionic compounds to be determined, and wherein in the membrane module there is a pressure equalization system integrated which at a pressure gradient occurring in operating condition between the measured medium and the probe interior is deformable in the direction of the pressure gradient.

2. The measuring probe according to claim 1, wherein all three layers are inseparably connected with one another forming a unitary membrane.

3. The measuring probe according to claim 1 wherein the first layer and the third layer are formed of a fluorized polymer, preferably of the same one.

4. The measuring probe according to claim 1 wherein the second layer is formed of a material highly permeable to the gases and/or non-ionic compounds to be determined, preferably a silicone caoutchouc.

5. The measuring probe according to claim 1 wherein a backing material, preferably a net of stainless steel, is embedded in the second layer.

6. The measuring probe according to claim 1 wherein the membrane is in a first end section of the membrane module rigidly fixed and sealed in such a way that the exchange of the gases and/or non-ionic compounds to be determined, between the measured medium and the probe interior, can in operating condition take place only through the membrane.

7. The measuring probe according to claim 1 wherein in the second end section of the membrane module, away from the membrane, there is an internal threading provided with corresponds to an external threading arranged on an electrode shaft supporting the internal body, allowing the membrane module to be screwed on the electrode shaft.

8. The measuring probe according to claim 1 wherein the pressure equalization system is arranged between the first end section supporting the membrane and the second end section of the membrane module provided with the internal threading.

9. The measuring probe according to claim 7, wherein the pressure equalization system is formed of biologically and/or chemically inert and thermally resistant, highly elastic material, preferably a vulcanizable fluoroelastomer.

10. The measuring probe according to claim 7 wherein the pressure equalization system is fashioned as a hose so fitted in the wall of the membrane module such that the outer surface of the membrane module will be free of unevennesses and/or cracks.

11. The measuring probe according to claim 1 used in a process for amperometric determination of oxygen in gas mixtures or fluids.

12. The measuring probe according to claim 1 used in a process for amperometric determination of chlorine or hydrogen in gas mixtures of fluids.

13. The measuring probe according to claim 8, wherein the pressure equalization system is fashioned as a hose so fitted in the wall of the membrane module such that the outer surface of the membrane module will be free of unevennesses and/or cracks.

* * * * *

UNITED STATES PATENT AND TRADEMARK OFFICE
CERTIFICATE OF CORRECTION

PATENT NO. : 5,239,257
DATED : August 24, 1993
INVENTOR(S) : Jorg Muller et al

It is certified that error appears in the above-indentified patent and that said Letters Patent is hereby corrected as shown below:

Col. 3, line 47, after "interior" insert --and reinforced by a backing material while fixed in the probe--.

Col. 5, line 33, change "∥" to --μ--.

Col. 8, line 6, change "fist" to --first--.

Signed and Sealed this

Nineteenth Day of April, 1994

Attest:

BRUCE LEHMAN

*Attesting Officer*  *Commissioner of Patents and Trademarks*